US010885231B2

(12) United States Patent
Matsumura et al.

(10) Patent No.: US 10,885,231 B2
(45) Date of Patent: Jan. 5, 2021

(54) MATERIAL GENERATION APPARATUS AND MATERIAL GENERATION METHOD

(71) Applicant: Hitachi, Ltd., Tokyo (JP)

(72) Inventors: Tadayuki Matsumura, Tokyo (JP); Yusuke Asari, Tokyo (JP)

(73) Assignee: HITACHI, LTD., Tokyo (JP)

( * ) Notice: Subject to any disclaimer, the term of this patent is extended or adjusted under 35 U.S.C. 154(b) by 876 days.

(21) Appl. No.: 15/622,104

(22) Filed: Jun. 14, 2017

(65) Prior Publication Data

US 2018/0018408 A1    Jan. 18, 2018

(30) Foreign Application Priority Data

Jul. 12, 2016  (JP) .................................. 2016-137833

(51) Int. Cl.
*G16C 20/30* (2019.01)
*G06F 30/00* (2020.01)
*G06N 3/08* (2006.01)

(52) U.S. Cl.
CPC ............. *G06F 30/00* (2020.01); *G06N 3/086* (2013.01); *G16C 20/30* (2019.02)

(58) Field of Classification Search
CPC ........ G06F 30/00; G06N 3/086; G16C 20/30; G16C 20/50
See application file for complete search history.

(56) References Cited

U.S. PATENT DOCUMENTS

| 5,600,570 A | * | 2/1997 | Imasato | ................. G16C 20/50 |
| | | | | 702/27 |
| 2012/0330632 A1 | * | 12/2012 | Oganov | ................. G16C 20/30 |
| | | | | 703/2 |

FOREIGN PATENT DOCUMENTS

| CN | 101655885 | * | 2/2010 | ............ G16C 20/30 |
| CN | 103218529 | * | 7/2013 | ............ G16C 20/30 |
| CN | 103246767 A | * | 8/2013 | ............ G16C 20/30 |
| CN | 103310049 A | * | 9/2013 | ............ G16C 20/30 |
| CN | 103324786 A | * | 9/2013 | ............ G16C 20/30 |
| EP | 1 962 234 A1 | * | 8/2008 | ............ G06N 3/00 |
| WO | 2007/071095 A1 | | 6/2007 | |
| WO | WO 2014/004370 A1 | * | 1/2014 | ............ G16C 20/30 |

* cited by examiner

*Primary Examiner* — Kandasamy Thangavelu
(74) *Attorney, Agent, or Firm* — Mattingly & Malur, PC

(57) ABSTRACT

A genetic algorithm controller that controls respective processes using a genetic algorithm is configured. The processes include generation of a crystal structure of an inorganic material, a mutation operation of a crystal structure, a crossing-over operation of a crystal structure, structural relaxation calculation of a crystal structure, calculation of a predictive value of an objective function, selection and weeding out of a crystal structure based on a predictive value of an objective function, observation of an objective function value of a crystal structure by first-principle calculation, update of a regression model based on a result of observing the objective function value, and end determination for a material generation process.

12 Claims, 15 Drawing Sheets

U: Lattice Vectors $(\vec{a}, \vec{b}, \vec{c})$
N: The number of atoms
$e_i$: Element type of atom i
$p_i$: Position of the atom i U: Lattice Vectors ($\vec{a}, \vec{b}, \vec{c}$)
N: The number of atoms
$e_i$: Element type of atom i
$p_i$: Position of the atom i

FIG. 12

| Element | Weight |
|---------|--------|
| H | 0.01 |
| He | 0.005 |
| Li | 0.02 |
| ... | ... |

FIG. 13

| Group | Elements |
|-------|----------|
| 1 | {Fe, Co, Ni, Mn} |
| 2 | {Li, Na, K, Rb} |
| 3 | {La Ce, Pr, Nd, Pm, Sm} |
| ... | ... |

FIG. 17

| The number of atoms | ELEMENT REPLACEMENT | LATTICE CONSTANT CHANGE | ATOM ADDITION | ATOM DELETION | CRYSTAL CROSSING |
|---|---|---|---|---|---|
| 100 | 0.2 | 0.2 | 0.2 | 0.2 | 0.6 |
| 50 | 0.3 | 0.3 | 0.5 | 0.5 | 0.3 |
| 10 | 0.5 | 0.5 | 0.3 | 0.3 | 0.1 |

US 10,885,231 B2

MATERIAL GENERATION APPARATUS AND MATERIAL GENERATION METHOD

BACKGROUND OF THE INVENTION

1. Field of the Invention

The present invention relates to a material generation apparatus and a material generation method.

2. Description of the Related Art

About 80 types of elements are treated in material science. However, eight million combinations are present in a whole ternary compound system even when x, y, and z are set to integers and restricted to x+y+z=10 in a ternary compound $A_xB_yC_z$. On the other hand, inorganic compound data up to a ternary system collected in a global inorganic crystal structure database currently corresponds to 76,000 cases, and the number of inorganic compounds, crystal structures of which are experimentally known, falls below 50,000 cases. Among these compounds, thermodynamics data such as generation energy is known in thousands of compounds, and a physical property is known in fewer compounds.

In general, material search aiming to realize an equivalent or surpassing property using another material with respect to a known property of a known material is a major theme in material research. Hitherto, an inorganic material having a new property has been accidentally discovered by individualistic experimental approach rather than being designed, and a lot of time is needed until practical application.

Recently, establishment of a systematic new material search scheme using a huge information processing technology of a computer has been actively progressing.

First-principle calculation for calculating an electronic state of an atom inside a crystal structure based only on a principle of quantum mechanics may quantitatively predict information such as a crystal structure, an electronic (magnetic) structure, a phonon state, free energy of formation, a dielectric constant, modulus of elasticity, etc. as a function of temperature or pressure by improvement in performance of the computer and an efficient calculation scheme. However, a problem of a high calculating cost still remains.

A problem of searching for a crystal structure of a new material using a material function as an objective value of an objective function is regarded as an optimization problem in which a huge degree of freedom of a compound is set to a search area when the search area is extended up to a multi-component system. An application of a metaheuristic such as a genetic algorithm is taken into account for a solution to this problem.

WO 2007/071095 A is present as a background art. This patent discloses a method of estimating a stablest structure of a crystal structure (a compositional formula is fixed to $A_xB_y$) of an inorganic compound using a genetic algorithm. In WO 2007/071095 A, a gene expression treats a lattice constant and coordinates of an atom as real numbers. The number of atoms of each element is given as a unique parameter. In addition, the number of atoms inside the crystal structure is fixed, and an operation in which the number of atoms increases or decreases is not present in a mutation operation. In addition, in a crossing-over operation of the crystal structure in WO 2007/071095 A, a crystal structure and a direction in which the crystal structure is connected are randomly selected, and matching is attempted such that the number of atoms after crossing-over does not change.

SUMMARY OF THE INVENTION

A technology disclosed in WO 2007/071095 A estimates a stablest structure of crystal structure, the number of atoms of which is fixed, designated by an input parameter, and may not be applied to a method of searching for a new crystal structure and a new material.

In a search for a new material using a genetic algorithm corresponding to a metaheuristic algorithm, there is a possibility that a large number of candidates for a solution to a crystal structure will be generated until the solution converges to a final solution. For example, when evaluation calculation of a magnetic value, etc. is attempted by first-principle calculation with respect to all the candidates for the solution to the crystal structure, a calculating cost excessively increases, which is impractical. There is a need to employ means for narrowing the candidates for the solution to the crystal structure by suppressing the calculating cost.

There is a need to newly define a mutation operator and a crossing-over operator applicable to a search for a new inorganic material using the genetic algorithm.

An object of the invention is to provide a material generation apparatus for searching for a new crystal structure that realizes an intended material function targeting an inorganic compound using a genetic algorithm, and a material generation method of reducing the amount of calculation for searching for the new crystal structure.

In order to solve the above issue, a material generation apparatus according to the present invention includes: a genetic algorithm controller that controls respective processes using a genetic algorithm, the processes including generation of a crystal structure of an inorganic material, a mutation operation of a crystal structure, a crossing-over operation of a crystal structure, structural relaxation calculation of a crystal structure, calculation of a predictive value of an objective function, selection and weeding out of a crystal structure based on a predictive value of an objective function, observation of an objective function value of a crystal structure by first-principle calculation, update of a regression model based on a result of observing the objective function value, and end determination for a material generation process; and a neighborhood set generator that includes a mutation unit that generates an N-fold crystal structure of a crystal structure, and adds an atom of a randomly selected element to coordinates at which a distance to a nearest neighbor atom is largest, a mutation unit that generates an N-fold crystal structure of a crystal structure, and deletes an atom of which a distance to a nearest neighbor atom is smallest, and a crossing-over unit that selects two crystal structures, divides each of the crystal structures by a section determined by random numbers, and combines the two crystal structures by one internal coordinate expression.

As another aspect of the present invention, in the material generation apparatus, gene data of a crystal structure used in each process controlled by the genetic algorithm controller includes a lattice vector ($a_v$, $b_v$, $c_v$) {hereinafter, vectors are described as $a_v$, with an index v}, lattice constants (a, b, c, α, β, γ), the number of atoms contained in a crystal lattice, and contained atom information obtained by repeating a combination of an element type and a position vector representing an atom position in a lattice vector expression for each atom contained in the crystal lattice a number of times corresponding to the number of contained atoms.

As another aspect of the present invention, the material generation apparatus further includes a neural network calculation unit that inputs an output of the structural relaxation calculation unit using a deep convolutional neural network configured such that a predictive value of an objective function is output by setting a calculation result of structural relaxation calculation of a crystal structure to an input, and outputs the predictive value of the objective function.

In order to solve the above issue, a material generation method includes: generating a current generation crystal structure set of an inorganic material by user definition or random generation at a time of start according to control of a genetic algorithm; generating a crystal structure of a new neighborhood set by a mutation operation of a crystal structure and a crossing-over operation of a crystal structure from the current generation crystal structure set; performing structural relaxation calculation on each crystal structure of the neighborhood set; calculating a feature amount with respect to each crystal structure after the structural relaxation calculation; calculating a predictive value of an objective function by inputting the calculated feature amount to a regression model; performing selection and weeding out of a crystal structure based on the predictive value of the objective function; repeating a loop from the generating of the crystal structure of the neighborhood set to the performing of the selection and weeding out of the crystal structure predetermined number of times; observing an objective function value by first-principle calculation or with reference to experimental data with respect to a crystal structure set; updating a regression model based on a result of observing the objective function value; and determining whether to end or continue processing by determining whether the result of observing the objective function value satisfies a predetermined condition.

According to the invention, it is possible to realize a material generation apparatus for searching for a new crystal structure which realizes an intended material function targeting an inorganic compound using a genetic algorithm. In addition, it is possible to provide a material generation method of reducing the amount of calculation for searching for the new crystal structure.

BRIEF DESCRIPTION OF THE DRAWINGS

FIG. 12 is a weight data table of element selection;

FIG. 13 is an element replacement group table;

FIG. 17 is a reference table for varying an occurrence probability of each operation according to the number of atoms inside the crystal structure when each mutation/crossing-over operation is performed;

DESCRIPTION OF THE PREFERRED EMBODIMENTS

Hereinafter, embodiments will be described using drawings.

First Embodiment

Figure 1:
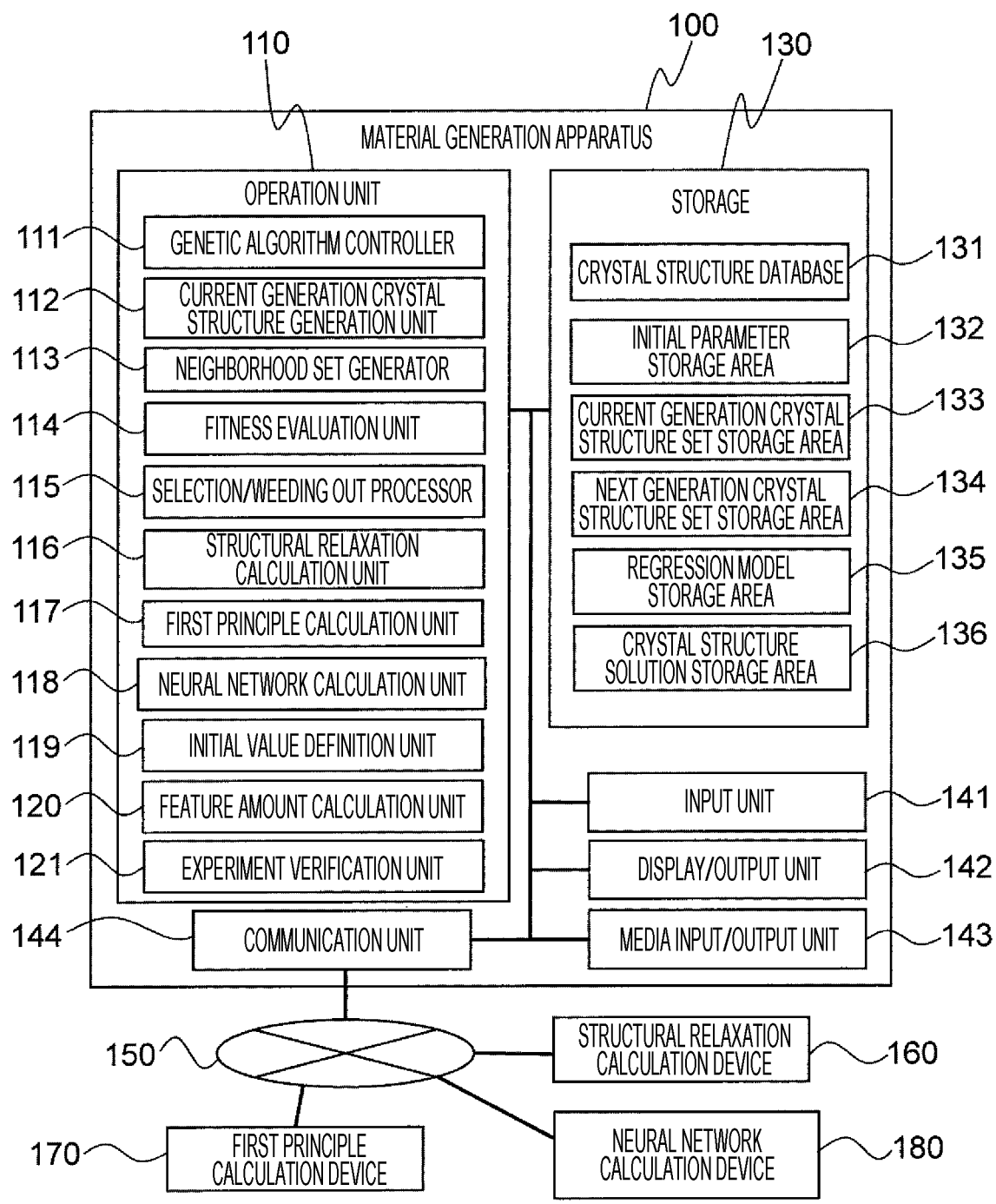
FIG. 1 is an example of a block diagram of a material generation apparatus according to a first embodiment of the invention.

FIG. 1 is an example of a block diagram of a material generation apparatus 100 according to a first embodiment.

The material generation apparatus 100 may be configured on a general-purpose computer, and a hardware configuration thereof includes an operation unit 110 including a central processing unit (CPU), a random access memory (RAM), etc., a storage 130 including a read only memory (ROM), a hard disk drive (HDD), a solid state drive (SSD) using a flash memory, etc., an input unit 141 including an input device such as a keyboard or a mouse, a display/output unit 142 including a display device such as a cathode ray tube (CRT) display, a liquid crystal display (LCD), or an organic electroluminescence (EL) display, and various output devices, a media input/output unit 143 that reads information of a portable storage medium having portability such as a CD-ROM or a universal serial bus (USB) memory or writes information thereto, and a communication unit 144 including a network interface card (NIC), etc.

The communication unit 144 is connected to a structural relaxation calculation device 160, a first principle calculation device 170, and a neural network calculation device 180 on the outside through a network 150.

The structural relaxation calculation device 160 has a configuration in which a structural relaxation calculation function is mounted on an external server. However, the structural relaxation calculation function may be mounted on the same computer as that of the material generation apparatus 100. The first principle calculation device 170 has a configuration in which a first-principle calculation function is mounted on an external server. However, the first-principle calculation function may be mounted on the same computer as that of the material generation apparatus 100. Further, the neural network calculation device 180 has a configuration in which a neural network function is mounted on an external server. However, the neural network function may be mounted on the same computer as that of the material generation apparatus 100.

The operation unit 110 implements respective function parts below by loading a material generation program (not illustrated) stored in the storage 130 in the RAM and executing the material generation program on the CPU. The operation unit 110 includes a genetic algorithm controller 111 that controls a whole material generation process using a genetic algorithm, a current generation crystal structure generation unit 112 that generates a predetermined number of (S) current generation crystal structures randomly or by user designation at the beginning of the material generation process, a neighborhood set generator 113 that generates a next generation crystal structure group by a mutation/crossing-over process, etc. from a current generation crystal structure group, a fitness evaluation unit 114 that evaluates fitness of each crystal structure, a selection/weeding out processor 115 that performs a selection/weeding out process of a crystal structure depending on the fitness, a structural relaxation calculation unit 116 that performs structural relaxation calculation on each crystal structure, a first principle calculation unit 117 that performs first-principle calculation on each crystal structure, a neural network calculation unit 118 that performs neural network calculation on each crystal structure, an initial value definition unit 119 for defining an initial parameter and a regression model used in the material generation process using the genetic algorithm by a user in advance and storing the defined initial parameter and regression model in the storage 130, a feature amount calculation unit 120 that calculates a feature amount corresponding to an observation value input to the regression model from a result of structural relaxation calculation, and an experiment verification unit 121 that retrieves corresponding experimental data from a crystal structure database or from experiment result data as an actual objective function value with respect to a crystal structure set.

The storage 130 includes a crystal structure database 131 of an inorganic compound, a crystal structure of which related to material search is previously experimentally known and to which an experimental value of a physical property, etc. is added, an initial parameter storage area 132 that stores an initial parameter used in a material generation process using a genetic algorithm defined by the user, a current generation crystal structure set storage area 133 that stores current generation crystal structure group data, a next generation crystal structure set storage area 134 that stores next generation crystal structure group data, a regression model storage area 135 that stores a regression model defined by the user, and a crystal structure solution storage area 136 that stores a crystal structure solution determined to be excellent at the time of end determination for the material generation process.

Figure 2A:
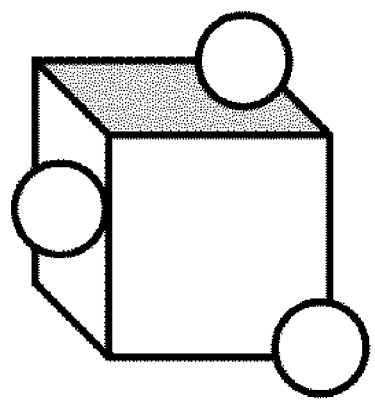
FIGS. 2A and 2B are an example of a crystal structure of an inorganic material targeted for material search in the first embodiment of the invention.
Figure 2B:
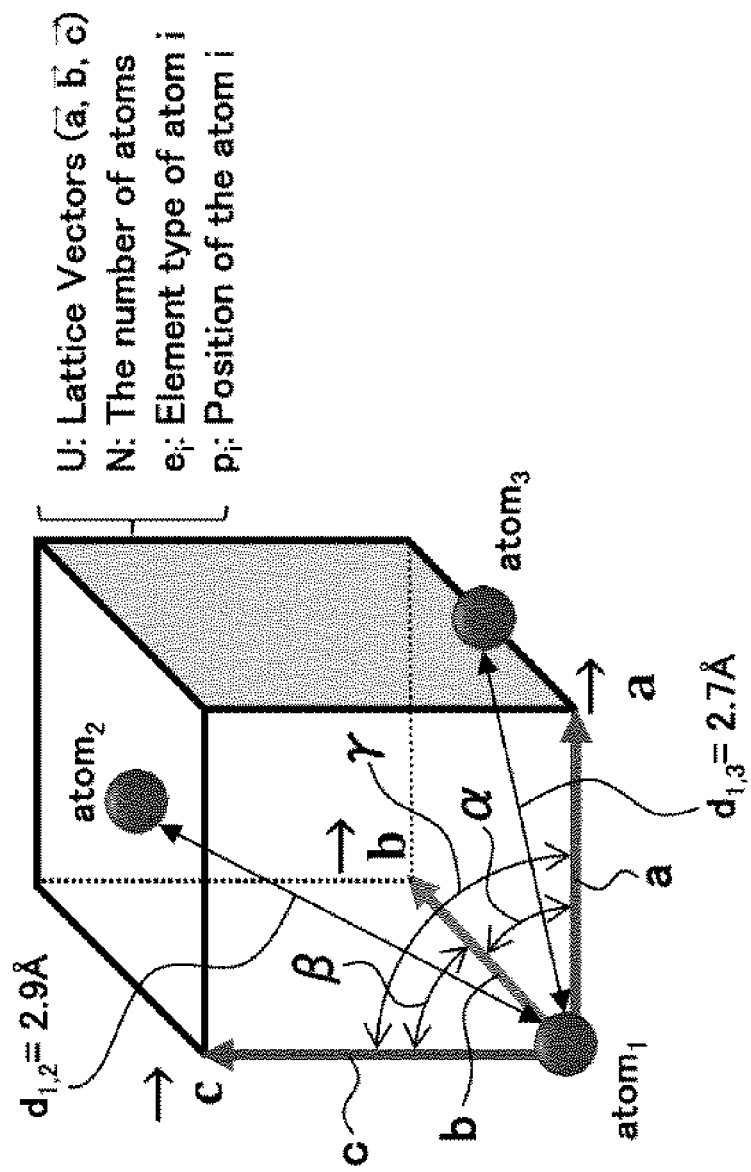

FIGS. 2A and 2B illustrate an example of a crystal structure of an inorganic material targeted for material search in the present embodiment. FIG. 2A defines a crystal model including three atoms, and FIG. 2B defines a crystal lattice vector $(a_v, b_v, c_v)$. Referring to lattice constants of the crystal structure, respective vector lengths correspond to a, b, and c, an angle formed by a lattice vector $(a_v, b_v)$ is defined as $\alpha$, an angle formed by a lattice vector $(b_v, c_v)$ is defined as $\beta$, and an angle formed by a lattice vector $(a_v, c_v)$ is defined as $\gamma$.

Figure 3:
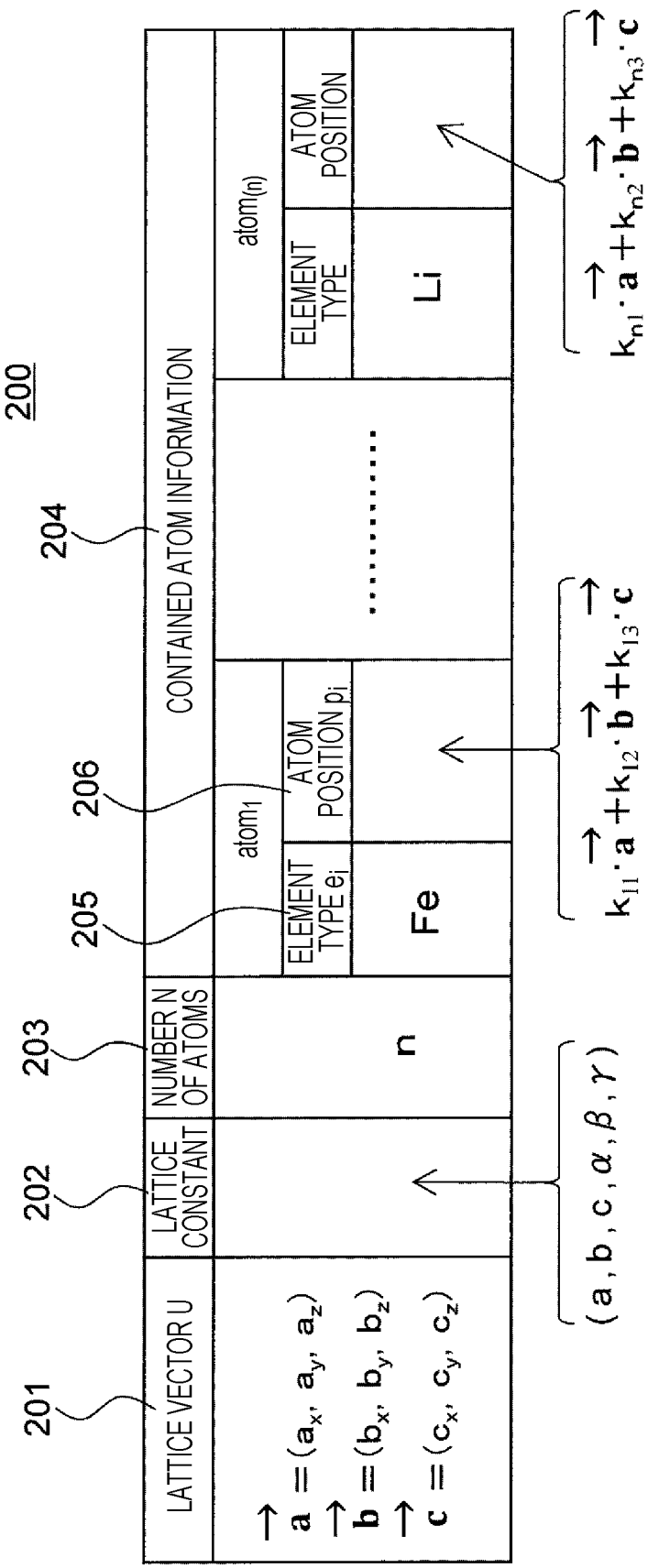
FIG. 3 is an example of a data record format of a gene employed in the first embodiment of the invention.

In the present embodiment, a gene expression, a crystal structure of a genetic algorithm is directly treated. A gene of a normal genetic algorithm uses an arrangement expression. However, a crystal structure of an inorganic compound is not suitable for an arrangement expression. Thus, for example, a gene 200 is expressed in a data record format illustrated in FIG. 3. In more detail, the data record format includes a lattice vector $(a_v, b_v, c_v)$ 201 corresponding to an expression by a reference Cartesian coordinate system (X, Y, Z) established in an analysis space on the computer, lattice constants (a, b, c, $\alpha$, $\beta$, $\gamma$) 202, the number N of atoms 203 contained in the crystal lattice, and contained atom information 204 obtained by repeating a combination of an element type 205 and a position vector 206 representing an atom position in a lattice vector expression for each atom contained in the crystal lattice a number of times corresponding to the number of contained atoms. The lattice constants 202 may be calculated from the lattice vector U 201, and thus may be excluded. In addition, this expression may treat crystals having different numbers of atoms in a united manner by having a variable length rather than arrangement of a fixed length used in a general genetic algorithm. In this way, it is important to allow material search in which the number of atoms is included in a search parameter.

Figure 4:
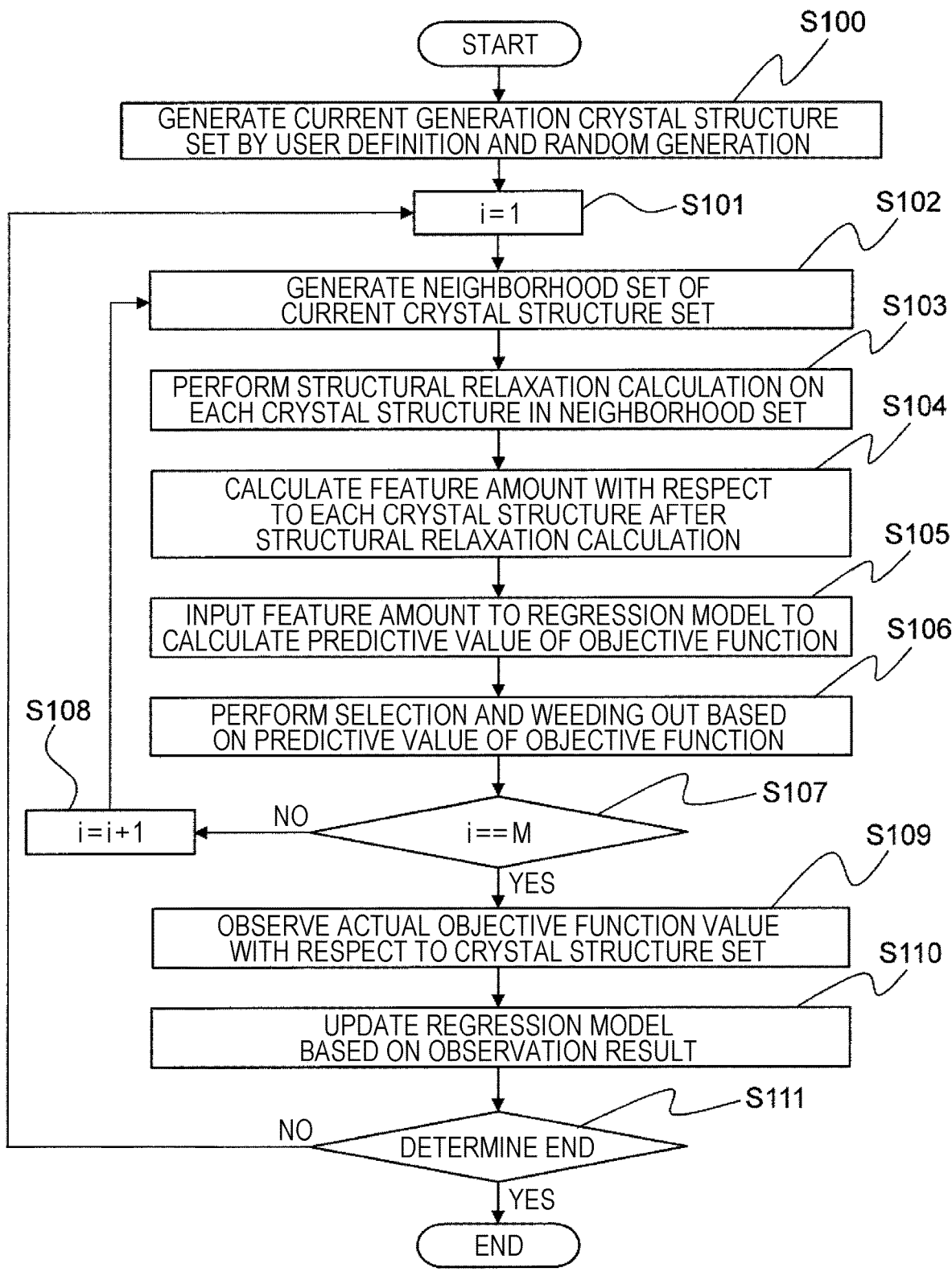
FIG. 4 is an example of a flowchart of a material generation process using a genetic algorithm according to the first embodiment of the invention.

FIG. 4 illustrates a flowchart of the material generation process using the genetic algorithm. The genetic algorithm controller 111 controls each function part of the material generation process.

In Step S100, the current generation crystal structure generation unit 112 generates an initial current generation crystal structure set. The number of generated crystal structures is S, which is defined by the user. In the case of random generation, each coordinate (or each lattice constant) of a lattice vector, the number of atoms, an element type of each contained atom, and an atom position are randomly determined according to random numbers defined in advance by the user and stored in the initial parameter storage area 132 to generate one current generation crystal structure, and the gene 200 of the crystal structure is stored in the current generation crystal structure set storage area 133. This operation is repeated S times to generate S crystal structure sets.

When a searched crystal structure is estimated to a certain degree, the user may intentionally generate an initial current generation crystal structure and include the generated initial current generation crystal structure in the S crystal structure sets. In this way, it is expected that a solution will more rapidly converge to an intended solution.

In addition, in the initial current generation crystal structure set, fitness described below is randomly generated (or intentionally assigning fitness by the user is allowed), added to the gene 200 of each current generation crystal structure, and stored in the current generation crystal structure set storage area 133.

In Step S101, an initial value 1 is input to a loop count variable i.

In Step S102, the neighborhood set generator 113 generates a neighborhood set of a current crystal structure set stored in the current generation crystal structure set storage area 133.

Herein, a description will be given of a mutation and crossing-over method of a crystal structure for an inorganic material search defined in the present embodiment.

Figure 5:
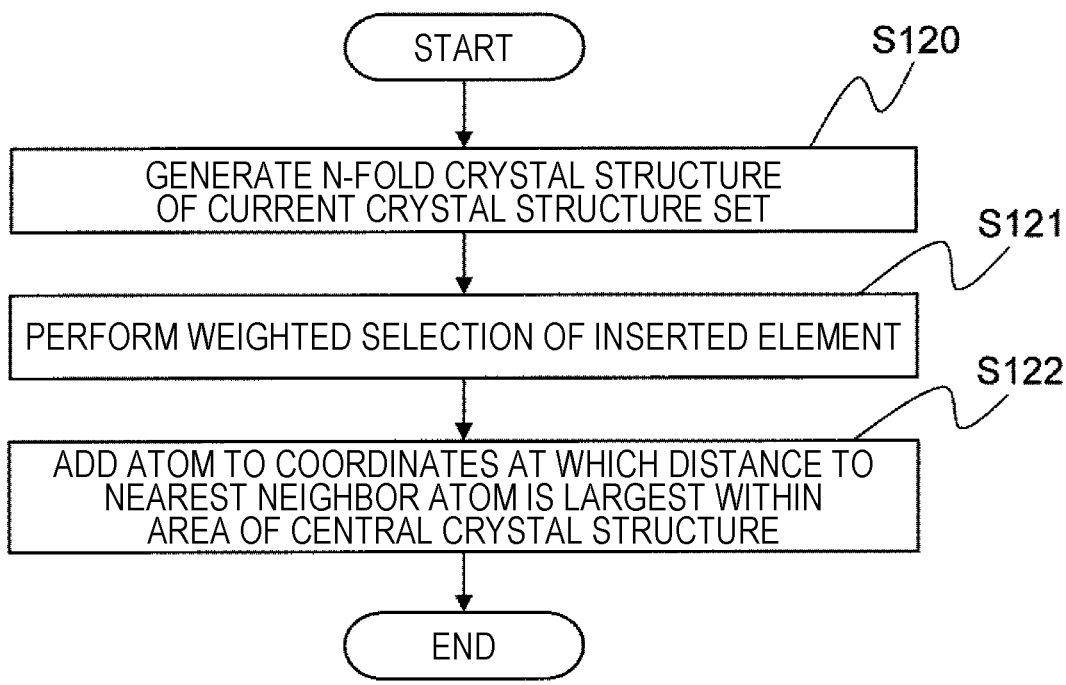
FIG. 5 is a flowchart illustrating a mutation method of adding a randomly selected atom to most available coordinates inside the crystal structure corresponding to one mutation method of the crystal structure.

A flowchart of FIG. 5 illustrates a mutation method of adding a randomly selected atom to most available coordinates inside the crystal structure corresponding to one mutation method of the crystal structure. An N-fold crystal structure (cell) mentioned in Step S120 will be described in FIGS. 14 and 15.

Figure 14B:
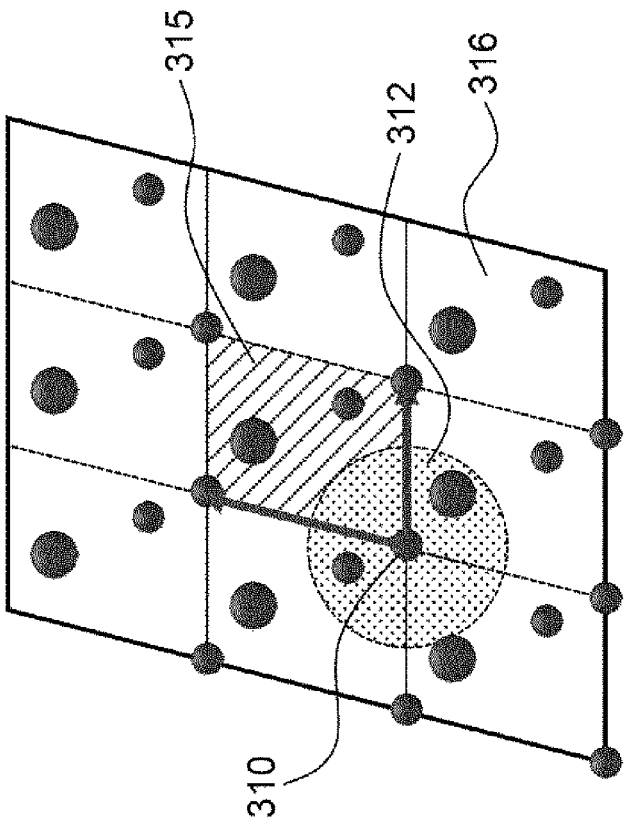
FIG. 14B is a diagram for description of an N-fold crystal structure enlarged by $N_a$, $N_b$, and $N_c$ times in respective axial directions of a crystal lattice.
Figure 14A:
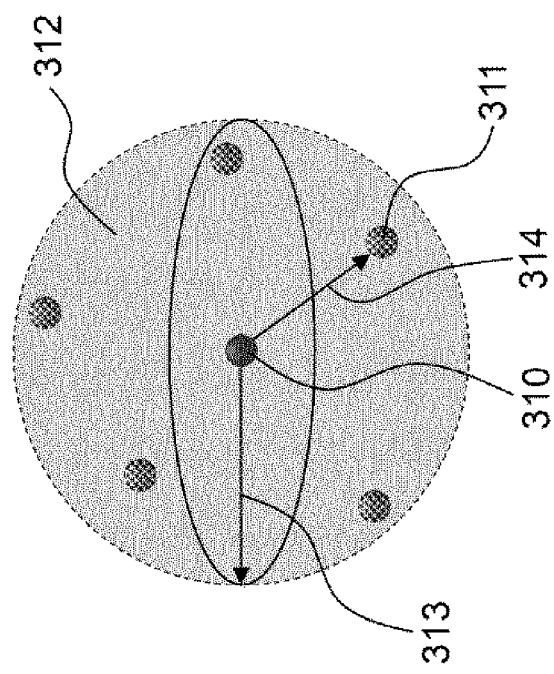
FIG. 14A is a diagram for description of definitions of a near neighbor atom 311, a cutoff radius 313, and a cutoff area 312 by presuming a sphere having a radius r313 around a certain atom 310.
Figure 15:
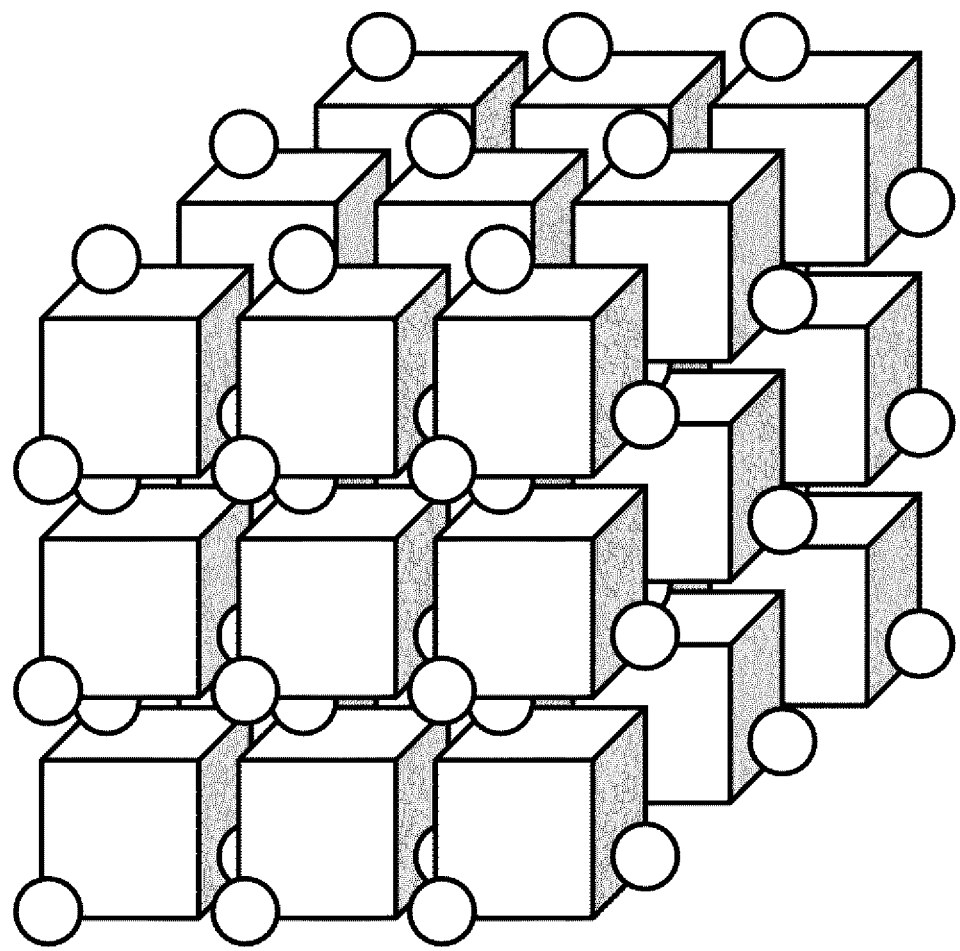
FIG. 15 is a diagram illustrating an example of an N-fold (3×3×3) crystal structure.

With regard to each atom present inside one crystal structure 315 (FIG. 14B is described in a two-dimensional (2D) cross section), a feature amount related to a distance between the atom and a near neighbor atom around the atom will be considered. In this instance, in order to define a near neighbor atom of a certain atom 310, a sphere having a radius r313 around the certain atom 310 is considered as in FIG. 14A, and an atom 311 inside the sphere is defined as a near neighbor atom 311 of the central atom 310. In addition, the radius considered for the near neighbor atom of the certain atom is referred to as a cutoff radius 313, and an area surrounded by the sphere is referred to as a cutoff area 312. Herein, when a feature amount related to an inter-atom distance 314 to the near neighbor atom is considered, it is inappropriate to consider only a single crystal structure. A reason therefor is that when only the single crystal structure is considered, the atom 310 close to a boundary of the crystal structure reaches the outside of the crystal structure considered by the cutoff area 312 as in FIG. 14B, and thus an atom, which should be originally considered as a near neighbor atom, may not be considered. In this regard, a crystal structure obtained by enlarging the crystal lattice by $N_a$, $N_b$, and $N_c$ times in respective axial directions is considered as in FIG. 14B such that cutoff areas of all atoms in the single crystal structure are included in the enlarged crystal structure. The enlarged crystal structure is referred to as an N-fold crystal structure 316. An example of an N-fold (3×3×3) crystal structure is illustrated in FIG. 15.

Returning to the description of Step S120 of the flowchart of FIG. 5, a crystal structure targeted for a mutation is selected from the current generation crystal structure set storage area 133 according to random numbers defined by the user, and an N-fold crystal structure of the crystal structure (see FIG. 15) is generated.

In Step S121, one element of an inserted atom is randomly selected at a possibility depending on weight data registered in response to each element from among elements registered in a weight data table for element selection illustrated in FIG. 12 with reference to the table, and an atom of the selected element is set to an inserted atom. The weight data table for element selection of FIG. 12 is defined in advance by the user, and registered in the initial parameter storage area 132.

In Step S122, a coordinate point at which a distance to a nearest neighbor atom is largest is searched for within an area of a central crystal structure of the N-fold crystal structure, a position thereof is determined to be a most available place in the central crystal structure, the atom of the element selected in Step S121 is added to the searched coordinate point, and data of the gene 200 is created as a crystal structure of a new mutation and stored in the next generation crystal structure set storage area 134.

Figure 6:
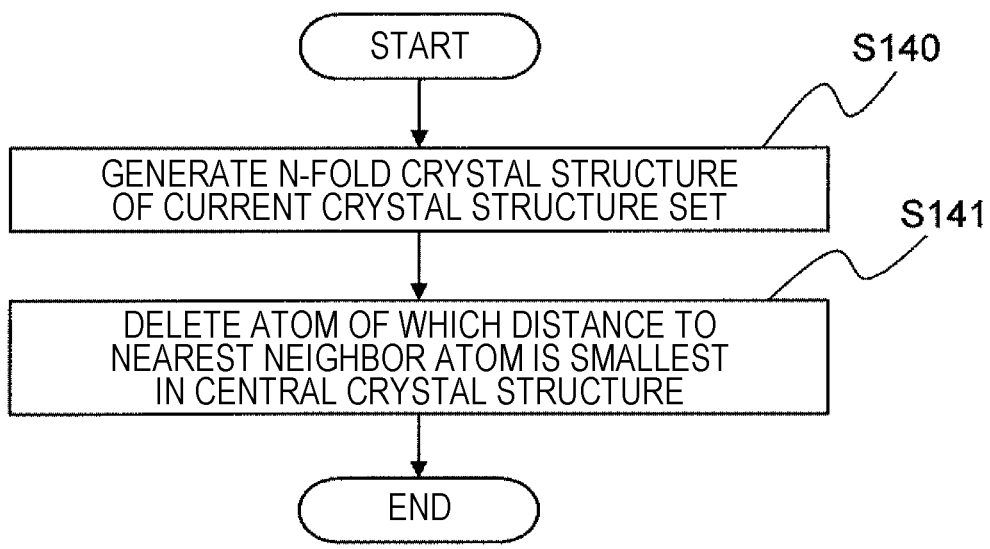
FIG. 6 is a flowchart illustrating a mutation method of deleting an atom present at a position at which atoms are recognized to be most densely congested inside the crystal structure corresponding to one mutation method of the crystal structure.

A flowchart of FIG. 6 illustrates a mutation method of deleting an atom present at a position at which atoms are recognized to be most densely congested inside the crystal structure corresponding to one mutation method of the crystal structure.

In Step S140, a crystal structure targeted for a mutation is selected from the current generation crystal structure set storage area 133 according to random numbers defined by the user, and an N-fold crystal structure of the crystal structure is generated.

In Step S141, atoms present inside an area of a central crystal structure in the N-fold crystal structure are successively selected, a distance from a selected atom to a nearest neighbor atom inside the N-fold crystal structure is evaluated, a selected atom, a distance to a nearest neighbor atom is smallest, or one of both atoms when an atom present at a distance between the selected atom and the nearest neighbor atom is inside the area of the central crystal structure is randomly selected and deleted, and data of the gene 200 is created as a crystal structure of a new mutation and stored in the next generation crystal structure set storage area 134.

Figure 7:
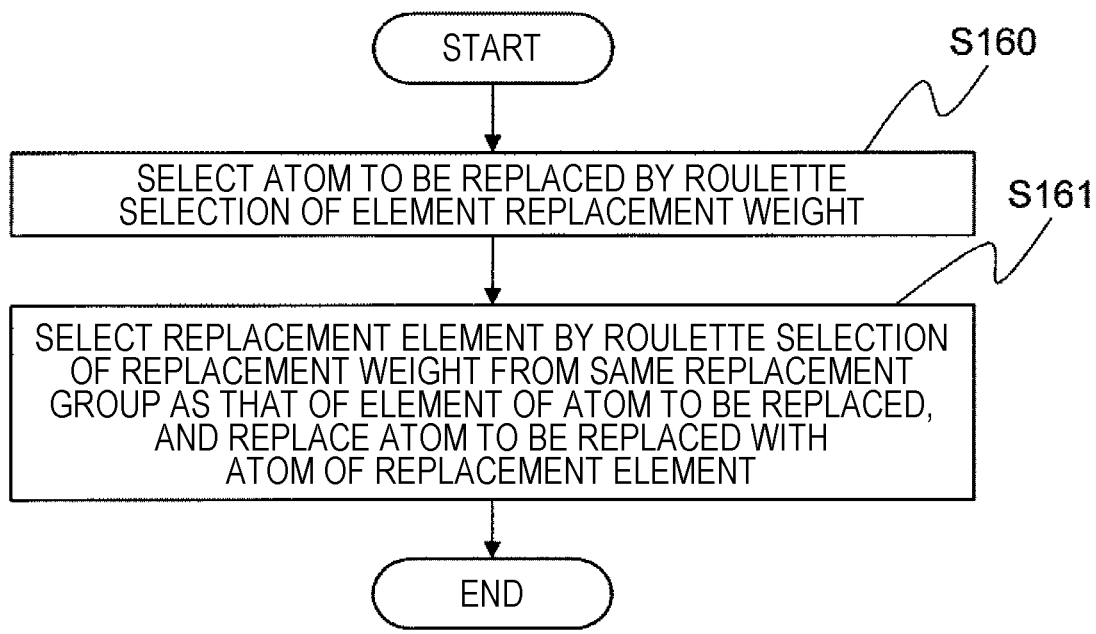
FIG. 7 is a flowchart illustrating a mutation method in which a certain atom inside the crystal structure is replaced with an atom of a different element corresponding to one mutation method of the crystal structure.

A flowchart of FIG. 7 illustrates a mutation method in which a certain atom inside the crystal structure is replaced with an atom of a different element corresponding to one mutation method of the crystal structure.

In Step S160, a crystal structure targeted for a mutation is selected from the current generation crystal structure set storage area 133 according to random numbers defined by the user, and an atom targeted for element replacement is randomly selected from the inside of the crystal structure with reference to a replacement weight depending on an element of each atom present inside the crystal structure from the weight data table for element selection of FIG. 12. The number of atoms targeted for element replacement is randomly selected when the number is one or more.

In Step S161, with regard to an element of the atom targeted for replacement selected in step S160, a replacement element is randomly selected such that an element replaceable with the element is selected with reference to an element replacement group table illustrated in FIG. 13, and another element inside a group in which the element targeted for replacement is included is selected with reference to the weight data table for element selection illustrated in FIG. 12. Then, data of the gene 200 is created as a crystal structure of a new mutation in which the atom of the crystal structure is replaced by an atom of the selected replacement element (when a plurality of atoms is targeted for replaced, each of the plurality of atoms is replaced) and stored in the next generation crystal structure set storage area 134.

The element replacement group table illustrated in FIG. 13 is defined in advance by the user and registered in the initial parameter storage area 132.

Figure 8:
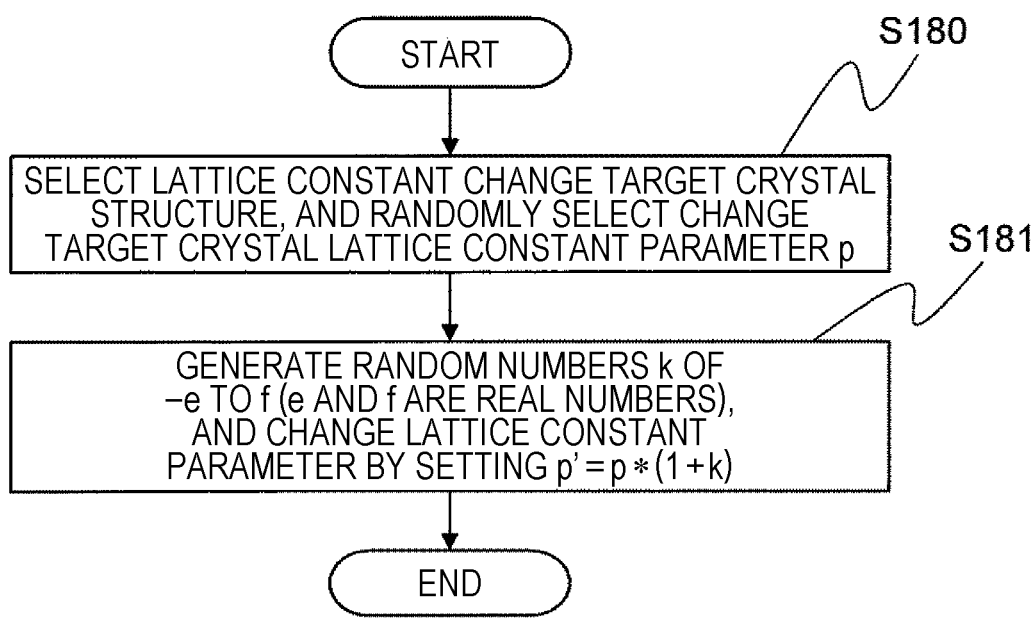
FIG. 8 is a flowchart illustrating a mutation method of changing a lattice constant of the crystal structure corresponding to one mutation method of the crystal structure.

A flowchart of FIG. 8 illustrates a mutation method of changing a lattice constant of the crystal structure corresponding to one mutation method of the crystal structure.

In Step S180, a crystal structure targeted for a mutation is selected from the current generation crystal structure set storage area 133 according to random numbers defined by the user, and a change target crystal lattice constant parameter $p \in \{a, b, c, \alpha, \beta, \gamma\}$ is randomly selected from a selected lattice constant change target crystal structure. The number of lattice constant parameters p is randomly selected when the number of one or more.

In Step S181, a random number k of −e to f (e and f are real numbers and defined in advance by the user) is generated with respect to the lattice constant parameter p selected in Step S180, and the lattice constant parameter is changed by setting p'=p*(1+k). Data of the gene 200 is created as a crystal structure of a new mutation in which the changed lattice constant parameter p' is set to a new lattice constant (a new lattice constant obtained by changing each of a plurality of lattice constant parameters p when the plurality of lattice constant parameters p is present) and stored in the next generation crystal structure set storage area 134.

Figure 9:
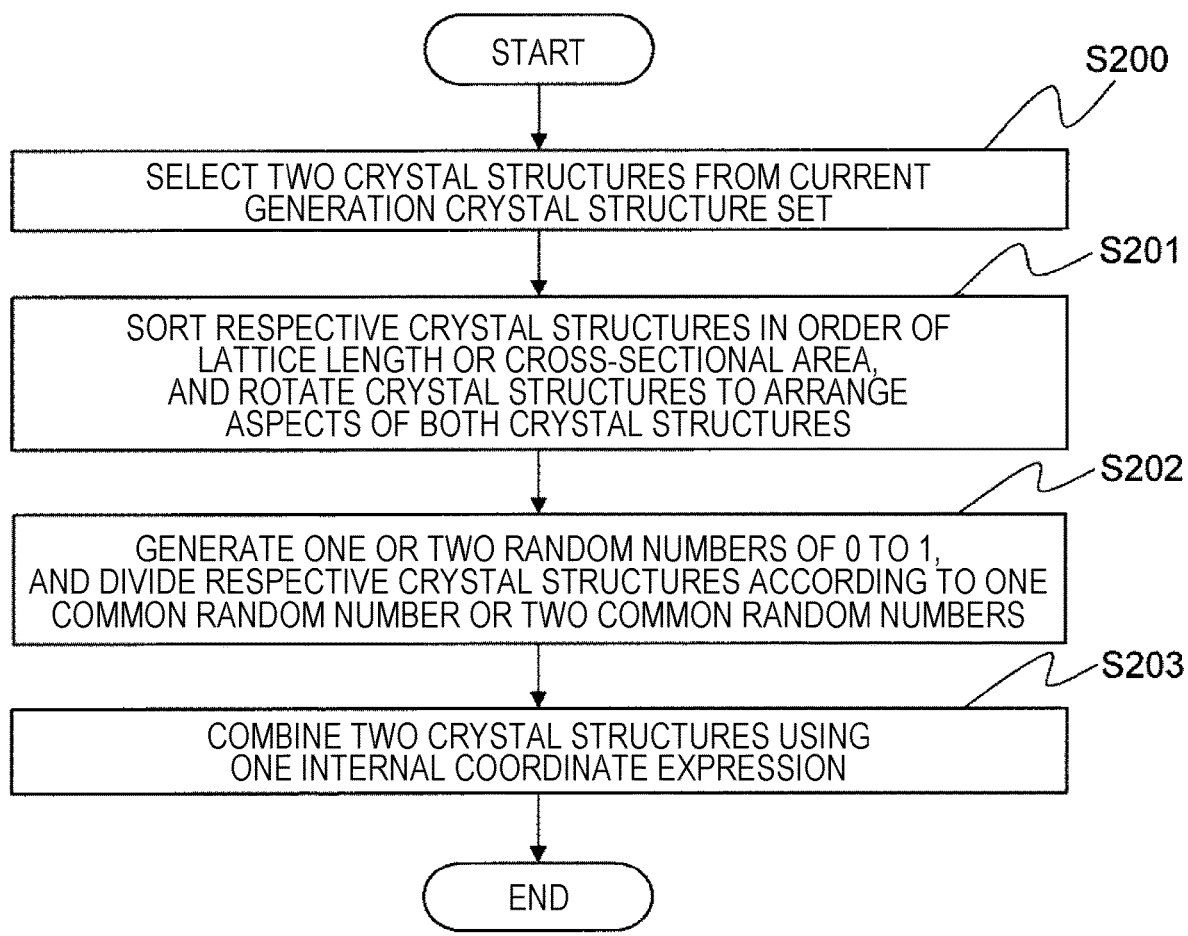
FIG. 9 is a flowchart illustrating a crossing-over method of the crystal structure.

A flowchart of FIG. 9 illustrates a crossing-over method of the crystal structure defined in the present embodiment. Crossing-over refers to a model in which a living organism leaves offspring through crossbreeding in a genetic algorithm, and refers to an operation of replacing a portion of an individual gene. Crossing-over may be regarded as a most important genetic manipulation in terms of a property thereof.

The crossing-over method of the crystal structure of the inorganic material of the present embodiment will be described using FIG. 10 and FIG. 11.

Figure 10:
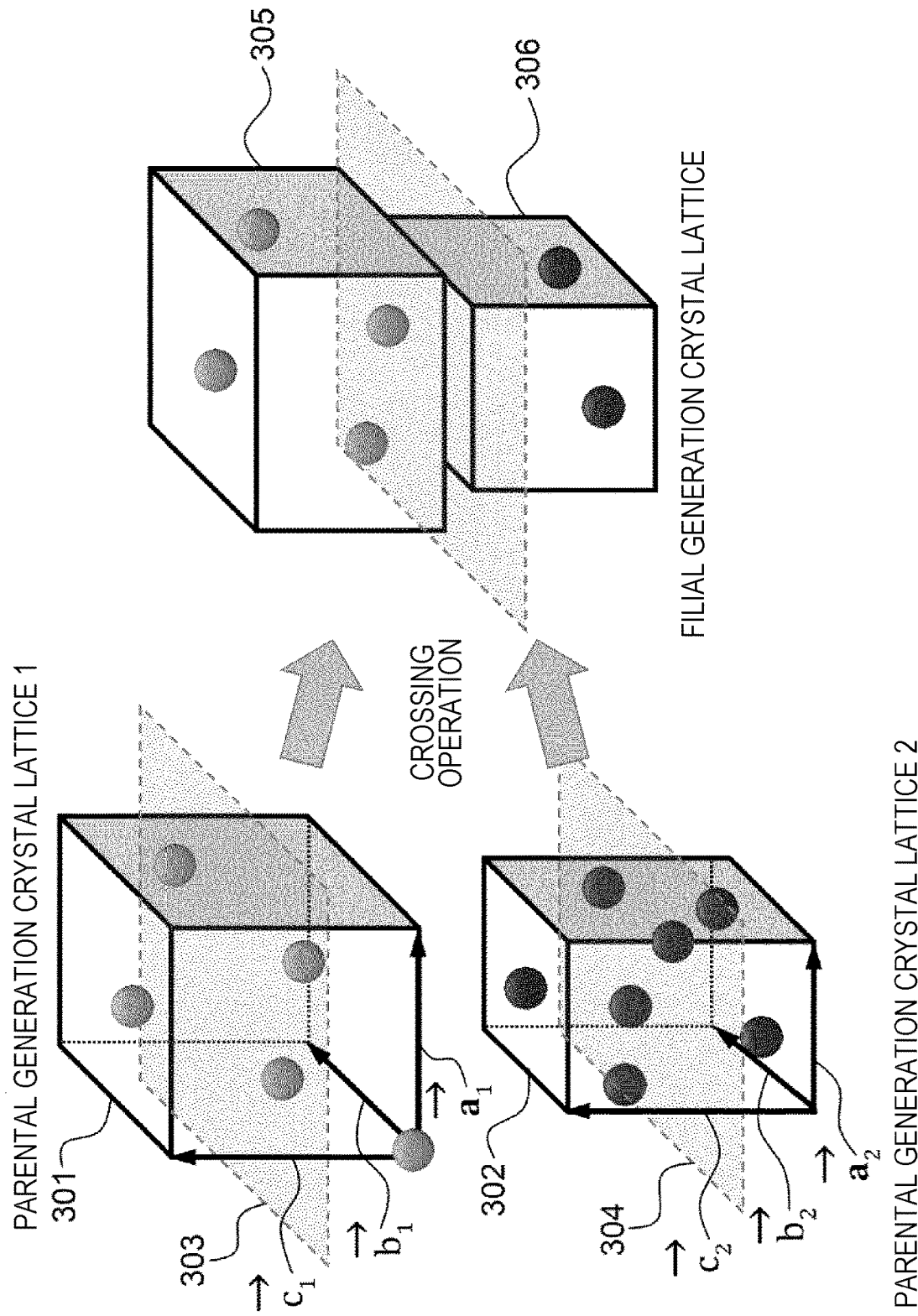
FIG. 10 is a diagram for description of a crossing-over operation of a parental generation crystal lattice 1 and a parental generation crystal lattice 2.
Figure 11:
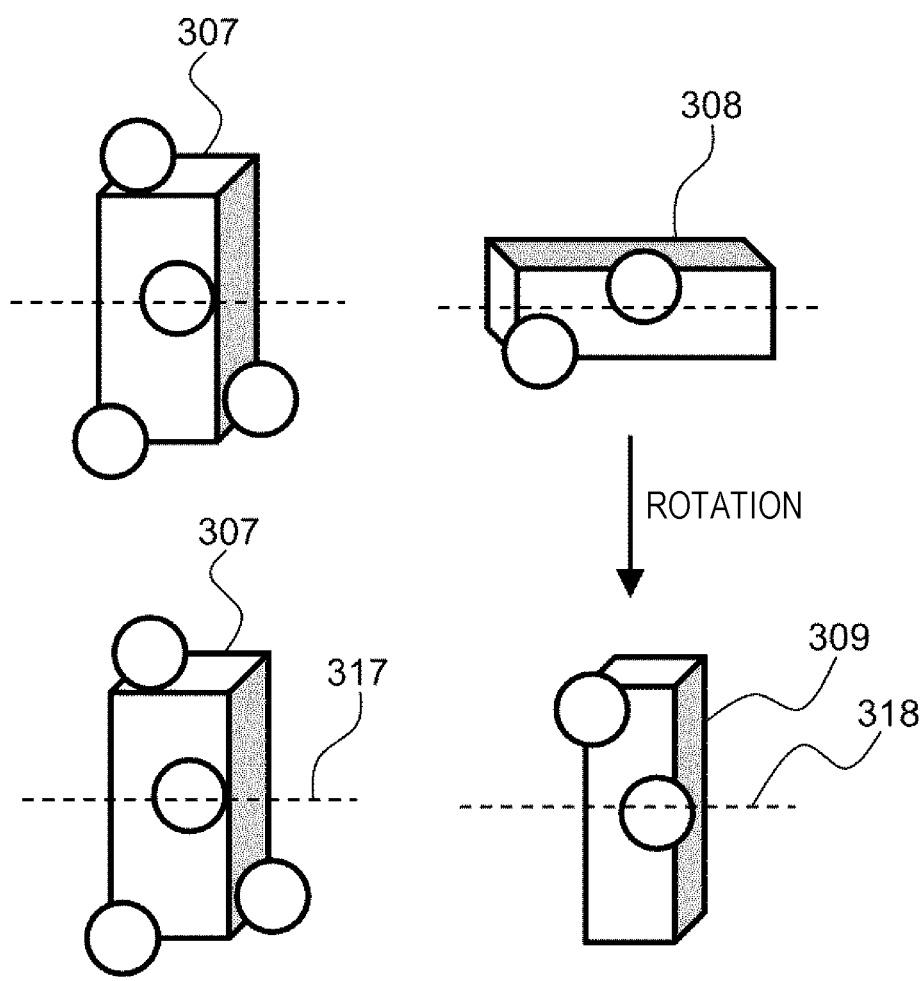
FIG. 11 is a diagram for description of determining a section by random numbers while rotating two crystal structures selected as crossing-over targets such that sort orders of lattice vector lengths or sort orders of cross-sectional areas are matched with each other.

In an example illustrated in FIG. 10, when an crossing-over operation of a parental generation crystal lattice 1 (301) and a parental generation crystal lattice 2 (302) is performed, the parental generation crystal lattice 1 (301) is cut by a section 303 parallel to a surface formed by a lattice vector ($a_{1v}$, $b_{1v}$), and the parental generation crystal lattice 2 (302) is cut by a section 304 parallel to a surface formed by a lattice vector ($a_{2v}$, $b_{2v}$). Herein, referring to the section 303 and the section 304, for example, a section is determined at a position that divides each of lattice vectors ($c_{1v}$, $c_{2v}$) at the same ratio of g:h by a common random number 1 of 0 to 1. Alternatively, for example, two random numbers of a random number 1 and a random number 2 of 0 to 1 may be used to determine the section 303 at a position that divides a lattice vector $c_{1v}$ of the parental generation crystal lattice 1 (301) at a ratio of $g_1:h_1$ according to the random number 1, and determine the section 304 at a position that divides a lattice vector $c_2$ of the parental generation crystal lattice 2 (302) at a ratio of $g_2:h_2$ according to the random number 2. One or two random numbers that determine a position of a section are defined in advance by the user and registered in the initial parameter storage area 132.

Then, an upper crystal structure 305 of the parental generation crystal lattice 1 (301) cut by the section 303 and a lower crystal structure 306 of the parental generation crystal lattice 2 (302) are joined to each other at the sections to form a crystal structure (filial generation crystal lattice) by a new crossing-over operation.

In the crossing-over method of the crystal structure of the inorganic material of the present embodiment, two target crystal structures defined in an analysis space on the computer are joined by matching aspects with each other as much as possible and forming sections. A description will be given in FIG. 11. Two crystal structures 307 and 308 selected as crossing-over targets are not immediately cut at sections in the same direction. Lattice vector lengths (a, b, c) of respective crystal structures are sorted in length order, or cross-sectional areas of a parallelogram formed by a combination of respective lattice vectors ($a_v$, $b_v$), ($b_v$, $c_v$), and ($a_v$, $c_v$) are sorted in size order. Then, the both crystal structures are disposed in the analysis space on the computer such that the sort orders of the lattice vector lengths or the sort orders of the cross-sectional areas sorted in the respective crystal structures are matched with each other. An example illustrated in FIG. 11 describes that sections 317 and 318 are determined by random numbers after the crystal structure 308 is rotated such that an aspect thereof is matched with an aspect of the crystal structure 307 and disposed as a crystal structure 309.

Returning to the description of the flowchart of the crossing-over method of FIG. 9, in Step S200, two crystal structures targeted for crossing-over are selected from the current generation crystal structure set storage area 133 according to random numbers defined by the user.

In Step S201, in the respective crystal structures targeted for crossing-over, a crystal structure is rotated such as the aspects of the both crystal structures are matched with each other by sorting orders of the lattice vector lengths or the cross-sectional areas and disposed in the analysis space on the computer.

In Step S202, one or two random numbers of 0 to 1 are generated, and the respective crystal structures are cut at sections dividing the crystal structures according to one common random number or two random numbers.

In Step S203, for example, when a divided crystal structure on a front side of a section is selected from two divided crystal structures obtained by cutting one of the both crystal structures cut in Step S202, a divided crystal structure on a rear side of a section is selected from two divided crystal structures obtained by cutting the other crystal structure since both sections are parallel to each other. Selection of a reverse combination may randomly occur.

Then, the selected divided crystal structures of the two crystal structures are joined at the sections to form a new crossing-over crystal structure. Referring to the new crossing-over crystal structure, data of the gene 200 that expresses the new crossing-over crystal structure (internal coordinate expression) is created using one lattice vector of the new crystal structure, and stored in the next generation crystal structure set storage area 134.

The process of Step S102 of the flowchart of FIG. 4 will be described again. A process of generating the neighborhood set of the current crystal structure set refers to a process of generating a new crystal structure by causing a mutation and crossing-over in a certain crystal structure of a current crystal structure set, and storing data of the gene 200 thereof in the next generation crystal structure set storage area 134. A possibility that each mutation/crossing-over will occur is defined in advance by the user and registered in the initial parameter storage area 132. In addition, the current generation crystal structure set storage area 133 stores gene data of S (defined by the user) current crystal structure sets. However, a selection method of selecting a crystal structure on which each mutation/crossing-over operation is performed is randomly performed. However, the selection method conforms to user definition.

For example, in a roulette selection method employed in a general genetic algorithm, $$p_j = \frac{f_j}{\sum_{k=1}^{S} f_k} \quad \text{[Equation 1]}$$

is set when a possibility of selecting a crystal structure j is denoted by $p_j$. Herein, $f_j$ denotes fitness (described below) of a crystal structure j. Referring to each crystal structure, in Step S105 described below, fitness is obtained at a point in time at which a predictive value of an objective function is calculated, added to gene data, and stored in the current generation crystal structure set storage area 133. However, at the time of starting the material generation process, in Step S100, fitness is randomly generated (or may be intentionally assigned by the user) in an initial current generation crystal structure set, added to the gene 200, and stored.

In the present embodiment, the each mutation/crossing-over operation is performed on the crystal structure selected by the selection method of the crystal structure defined by the user according to a possibility defined by the user. However, an occurrence probability of each of the operations is changed depending on the number of atoms inside the crystal structure as illustrated in a table of FIG. 17. An interpolation value and an extrapolation value of an occurrence probability of each operation are applied in the case of a value other than the number of atoms indicated in the table of FIG. 17.

In Step S102, after a new crystal structure by S' (the number is defined by the user)—S mutation/crossing-over operations is generated from S (the number is defined by the user) current crystal structure sets stored in the current generation crystal structure set storage area 133, a crystal structure stored in the current generation crystal structure set storage area 133 corresponding to a parent is moved to the next generation crystal structure set storage area 134 to form a neighborhood set together with the crystal structure generated by the mutation/crossing-over operations. In addition, a crystal structure remaining in the current generation crystal structure set storage area 133 on which no mutation/crossing-over operation is performed is moved to the next generation crystal structure set storage area 134. Therefore, gene data of S' crystal structures are stored in the next generation crystal structure set storage area 134.

In Step S103, structural relaxation calculation is performed on each crystal structure in the neighborhood set stored in the next generation crystal structure set storage area 134.

The structural relaxation calculation refers to a method of calculating coordinates or a crystal structure (cell) of an atom from a force received by the atom by inputting coordinates of an atom in the crystal structure. In this calculation, coordinates of an input atom are set to an initial position to calculate a force acting on the atom, the atom is automatically moved in a direction of the force, and the atom is simply moved in a direction in which the force decreases. Even though proper dynamic motion is not calculated as in a case in which an equation of motion is solved, a crystal structure (cell) relieved to a stablest or semi-stable structure is calculated. The calculation is also referred to as structural optimization calculation. The structural relaxation calculation uses a known program.

A crystal structure generated by each mutation/crossing-over operation in S102 or randomly in Step S100 defines a new crystal structure by mechanically determining a position of an atom. However, in a current crystal structure, there is a possibility that a position of an atom may be present at a position greatly different from that at the time of generating the crystal structure. The difference is approximately determined by the structural relaxation calculation, and data of the gene 200 of the crystal structure is correctly by a correction result of the crystal structure close to reality.

In Step S103, the structural relaxation calculation unit 116 sends gene data of each crystal structure in the neighborhood set stored in the next generation crystal structure set storage area 134 to the structural relaxation calculation device 160 to request calculation, or request calculation from a structural relaxation calculation program executed on the same computer as that of the material generation apparatus 100, receives a structural relaxation calculation result, and corrects the gene data from the calculation result. In addition, the crystal structure created in Step S100 among crystal structures moved from the current generation crystal structure set storage area 133 to the next generation crystal structure set storage area 134 is subjected to structural relaxation calculation in Step S103.

In Step S104, the fitness evaluation unit 114 calculates a feature amount of a regression model defined by the user.

For example, when an object of the material generation process of the present embodiment is to "search for a crystal structure of an inorganic material having a magnetic value of 3.5 μB", the user defines a regression model by setting a "magnetic value" as an objective variable, and giving every variable, a geometric feature amount of which of a crystal structure considered to be related to a physical phenomenon of magnetism is conceivable, as an explanatory variable, and the regression model is stored in the regression model storage area 135 in advance by the initial value definition unit 119. A multivariate regression model, a decision tree, a neural network, etc. is considered as the regression model.

For example, a multivariate regression model shown in Equation 2 is defined.

"magnetic value" (objective variable)=$\beta_1+\beta_2\times$"number of atoms in crystal" (feature amount 1)+$\beta_3\times$"average value of all inter-atom distances" (feature amount 2)+ . . . +$\beta_{n+1}\times$(feature amount $n$)   (Equation 2)

Herein, temporary values are set as the coefficients $\beta_1$, $\beta_2$, $\beta_3$, ... $\beta_{n+1}$ with reference to former experimental data, etc. An objective function for obtaining the objective variable "magnetic value" is configured. The feature amount 1 ... the feature amount n correspond to feature amounts related to geometric information, phase information, the number of valence electrons, etc.

Figure 16:
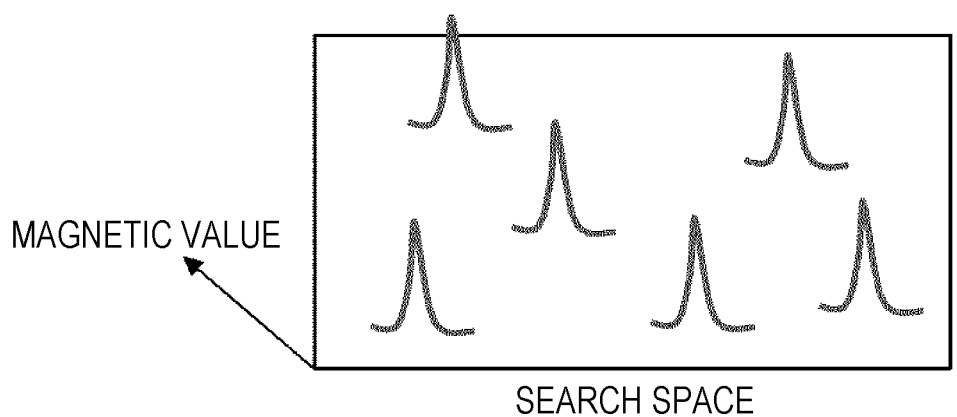
FIG. 16 is a diagram illustrating an example of a magnetic value observed in a search space when an actual material is measured.

When an actual material is measured, it is expected that the magnetic value will correspond to a search space in which peaks intermittently rises and most of the space is 0 as illustrated in FIG. 16. There is difficulty in solidly modeling such a phenomenon in a single regression model. In this regard, it is desirable to configure a plurality of regression models rather than performing modeling by one regression model as in the above description. For example, a random forest that configures a model by a plurality of decision trees improves solidity of the model by setting an average value of predictive values of the respective decision trees to a predictive value. However, when the case of FIG. 16 is presumed, it may be inappropriate to set an average to a predictive value. A case in which a maximum value, a minimum value, or a median value is appropriate may be considered depending on the problem.

First, a description will be given of a case in which a single regression model is configured. The feature amount calculation unit 120 calculates the feature amounts (the feature amount 1, . . . , the feature amount n) of the regression model shown in Equation 2 with respect to each crystal structure after the structural relaxation calculation in Step S104.

In Step S105, the fitness evaluation unit 114 inputs the feature amounts (the feature amount 1, . . . , the feature amount n) calculated in Step S104 to the regression model shown in Equation 2, and calculates a magnetic value (a predictive value of an objective function) corresponding to an objective variable of this case for each crystal structure. When the model includes the above-described plurality of regression models, a maximum value, a minimum value, or a median value may be employed in addition to an average value of all the models as the predictive value of the objective function.

The user defines a fitness function f (a predictive value of a magnetic value) in which a greater fitness output value is obtained as a predictive value of a magnetic value of each crystal structure herein approaches 3.5 μB, and a maximum fitness output is obtained at 3.5 µB, thereby calculating fitness of each crystal structure.

In Step S106, the selection/weeding out processor 115 selects and leaves S crystal structures from crystal structures having values close to the objective value "magnetic value 3.5 µB" based on the predictive value of the objective function of each crystal structure calculated in Step S105, adds the predictive value and the fitness of the objective function calculated in Step S105 to data of the gene 200 of the selected crystal structures, and stores the data in the current generation crystal structure set storage area 133 which is cleared in advance. In this way, S new current generation crystal structure sets are obtained. Crystal structures left in the next generation crystal structure set storage area 134 are weeded out.

When the loop count variable i reaches a predetermined loop number M defined in advance by the user in Step S107, the operation proceeds to Step S109. When the loop count variable i does not reach the loop number M, the loop count variable i is incremented by 1 in Step S108, and the processes are repeated from Step S102.

In Step S109, the first principle calculation unit 117 performs first-principle calculation on each crystal structure of the S crystal structure sets stored in the current generation crystal structure set storage area 133 or the selected crystal structures. When only a particular crystal structure is selected as a calculation target, for example, when a crystal has been previously calculated in the past, it is efficient to read a value from a database without performing calculation again. Thus, in such a case, use for omitting the first-principle calculation with respect to the crystal structure is considered. The first principle calculation unit 117 sends gene data of each crystal structure to the first principle calculation device 170 to request calculation, or request calculation from a first-principle calculation program executed on the same computer as that of the material generation apparatus 100 to receive a first-principle calculation result. The first-principle calculation corresponds to a scheme of calculating an electronic state of an atom which determines most substance properties, and may observe a current crystal structure and magnetic structure. A known program is used as the first-principle calculation program.

In Step S109, the experiment verification unit 121 is started when the objective variable of the objective function is not a magnetic value and is another physical property, and may not be calculated by the first-principle calculation. The experiment verification unit 121 inputs an experiment result obtained by experiment verification as an observation value of the objective function, or retrieves and inputs an appropriate observation value from the crystal structure database 131 that records experimental data of a former similar crystal structure.

In Step S110, the genetic algorithm controller 111 updates the regression model based on the observation value of the objective function obtained in Step S109.

In more detail, for example, when the regression model shown in Equation 2 is defined, an observation value of a current crystal structure and magnetic structure with respect to each crystal structure is obtained in Step S109, and thus data of the gene 200 of the crystal structure is corrected. Based thereon, the feature amounts (the feature amount 1, . . . , the feature amount n) are calculated and input to the regression model, and the observation value of the magnetic structure is input to the objective variable "magnetic value", thereby updating the regression model.

In Step S111, for example, when a certain crystal structure calculated in Step S109 is found in Step S110, and an error amount between a magnetic value (objective function value) obtained from an observation value of a magnetic structure of the crystal structure and a desired value "magnetic value 3.5 µB" is less than or equal to a predetermined threshold value, end determination of ending the material generation process is performed. When end determination is performed, for example, the genetic algorithm controller 111 stores data of the gene 200 of the crystal structure with which the error amount with respect to the desired value is less than or equal to the predetermined threshold value in the crystal structure solution storage area 136, and ends the material generation process.

When the crystal structure is not found in Step S111, the operation proceeds to Step S101, and a process of repeating Steps S102 to S107 again is continued.

In addition, when it is determined that an error amount between no objective function value and the desired value is less than or equal to the predetermined threshold value a predetermined number of times or more in end determination of Step S111, a determination process of stopping and ending the material generation process may be employed.

In addition, when a crystal structure with which an objective function value is closest to the desired value (fitness is highest) is stored in Step S110, and it is determined that search is not improved since an error amount between an objective function value of a current crystal structure and the desired value is regarded as larger than an error amount between an objective function value of a previous crystal structure and the desired value at the time of end determination after a predetermined number of times in end determination of Step S111, a determination process of stopping and ending the material generation process may be employed.

Second Embodiment

Figure 18:
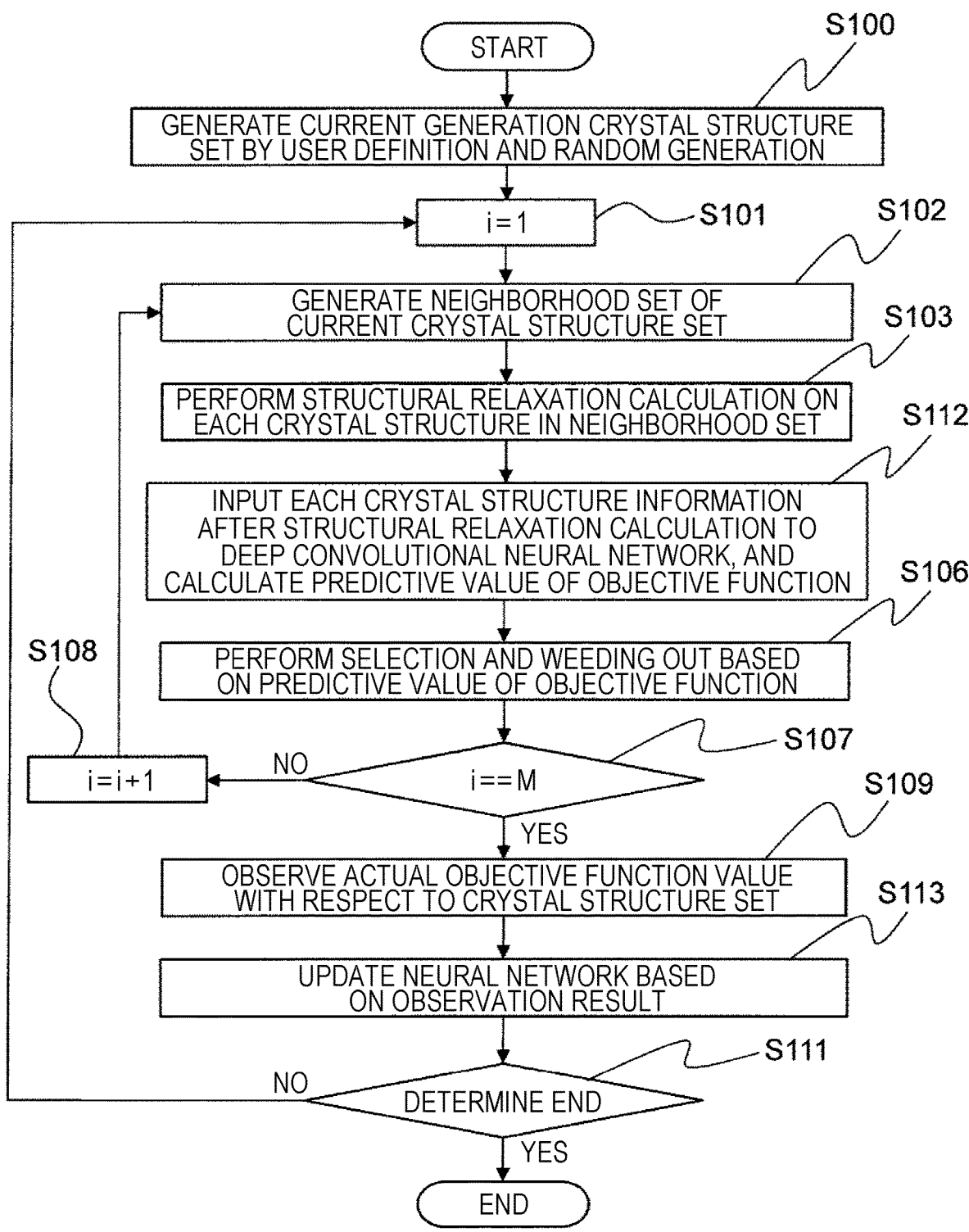
FIG. 18 is an example of a flowchart of a material generation process using a genetic algorithm according to a second embodiment of the invention.

FIG. 18 illustrates a flowchart of a material generation process according to a second embodiment. A difference from the material generation process of the first embodiment illustrated in FIG. 4 is that, without the user defining a regression model, a crystal structure is input to a neural network, feature amount extraction is performed in the neural network, and the neural network is set to a regression model.

An issue in creation of the regression model of the crystal structure employed in the first embodiment is definition of an excellent feature amount, and the excellent feature amount is rarely known. Therefore, there is difficulty in creating an accurate regression model.

In an image processing field, validity of a method of inputting image data to a neural network without change, and performing feature amount extraction therefrom without a person defining a feature amount is indicated. Therefore, the present embodiment employs means for inputting a crystal structure to a neural network, and automatically extracting and returning a feature amount.

A method of inputting a crystal structure to a neural network is not generally known. In the present embodiment, a method of inputting an image is extended by perceiving the image as 2D arrangement, and perceiving a crystal structure as three-dimensional (3D) arrangement, and the crystal structure is input. As an important point here, in order to match input dimensionality of the neural network, or in order to match a relative meaning of each point, rather than inputting the crystal structure without change, an N-fold cell is divided by an equally spaced grid defined by the user, a 3D lattice around each atom is considered, and the 3D lattice is input.

Processes of Steps S100 to S103 of the flowchart of FIG. 18 are similar to processes of the flowchart of FIG. 4 of the first embodiment, and thus a description thereof will be omitted.

In Step S112, the present embodiment uses a deep convolutional neural network configured such that an input corresponds to one-dimensional (1D) arrangement data created from a crystal structure, and an output corresponds to a magnetic value which is an objective variable.

Figure 19:
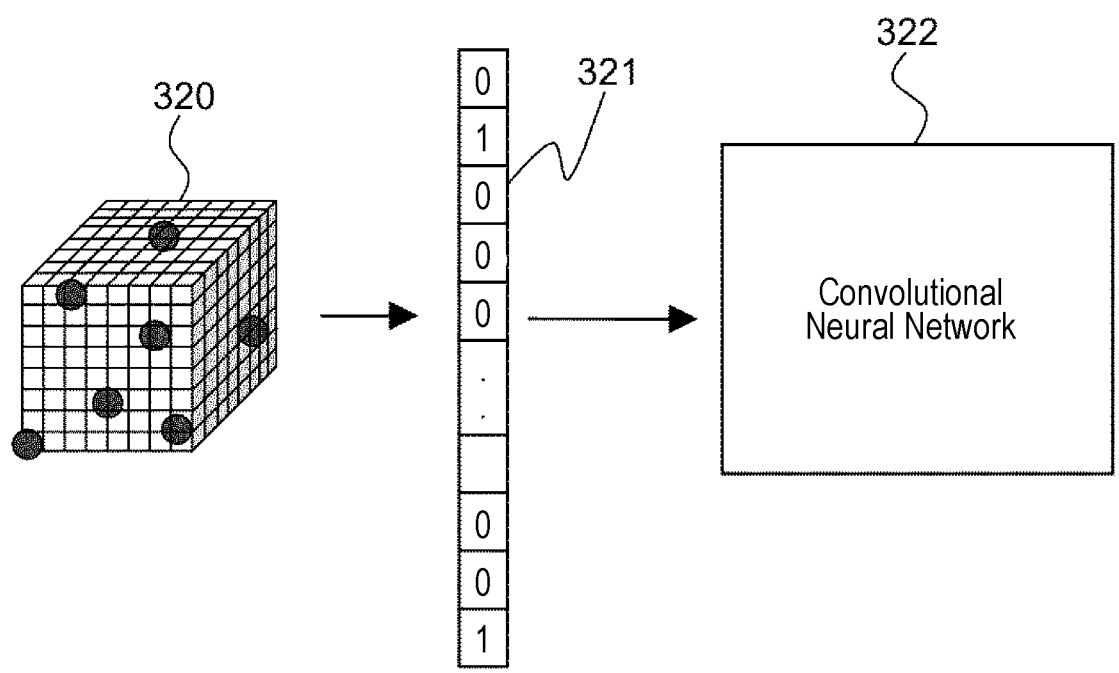
FIG. 19 is a diagram for description of a method of inputting a crystal structure to a neural network.

An N-fold cell (crystal structure) of each crystal structure is created as illustrated in FIG. 19 using each crystal structure, on which structural relaxation calculation is performed in Step S103, as an input target, and divided by an equally spaced grid defined by the user (320). A cube around a grid including each atom which is included in a target crystal structure is considered, data of a set of feature amounts of each atom such as an electronic number in addition to the presence/absence (0/1) of an atom as data of each cube in an grid arrangement order is converted into 1D arrangement data 321, and the 1D arrangement data is input to a deep convolutional neural network 322. An output of the deep convolutional neural network 322 is acquired as a predictive value of an objective function.

In Step S112, the neural network calculation unit 118 creates the 1D arrangement data 321 from gene data of each crystal structure in the neighborhood set stored in the next generation crystal structure set storage area 134, sends the 1D arrangement data to the neural network calculation device 180 to request calculation or request calculation from a neural network program executed on the same computer as that of the material generation apparatus 100, and receives a calculation result (a predictive value of an objective function). A known program is used as a deep convolutional neural network.

Processes of Steps S106 to S109 of the flowchart of FIG. 18 are similar to processes of the flowchart of FIG. 4 of the first embodiment, and thus a description thereof will be omitted.

In Step S113, the genetic algorithm controller 111 updates a neural network (regression model) based on the observation value of the objective function obtained in Step S109.

What is claimed is:

1. A material generation apparatus comprising:
a genetic algorithm controller that controls respective processes using a genetic algorithm, the processes including generation of a crystal structure of an inorganic material, a mutation operation of a crystal structure, a crossing-over operation of a crystal structure, structural relaxation calculation of a crystal structure, calculation of a predictive value of an objective function, selection and weeding out of a crystal structure based on a predictive value of an objective function, observation of an objective function value of a crystal structure by first-principle calculation, update of a regression model based on a result of observing the objective function value, and end determination for a material generation process; and
a neighborhood set generator that includes
a mutation unit that generates an N-fold crystal structure of a crystal structure, and adds an atom of a randomly selected element to coordinates at which a distance to a nearest neighbor atom is largest,
a mutation unit that generates an N-fold crystal structure of a crystal structure, and deletes an atom of which a distance to a nearest neighbor atom is smallest, and
a crossing-over unit that selects two crystal structures, divides each of the crystal structures by a section determined by random numbers, and combines the two crystal structures by one internal coordinate expression.

2. The material generation apparatus according to claim 1, wherein
the neighborhood set generator further includes
a mutation unit that selects a replacement target atom of a selected crystal structure by element replacement-weighted roulette selection, selects a replacement element by replacement-weighted roulette selection from the same replacement group as a replacement group of an element of the replacement target atom, and replaces the replacement target atom by an atom of the replacement element.

3. The material generation apparatus according to claim 1, wherein
the neighborhood set generator further includes
a mutation unit that selects a lattice constant change target crystal structure to randomly select a change target crystal lattice constant parameter p, generates a random number k of −e to f (e and f are real numbers), and changes the lattice constant parameter by setting p'=p*(1+k).

4. The material generation apparatus according to claim 1, wherein
gene data of a crystal structure used in each process controlled by the genetic algorithm controller includes a lattice vector ($a_v$, $b_v$, $c_v$), lattice constants (a, b, c, α, β, γ), the number of atoms contained in a crystal lattice, and contained atom information obtained by repeating a combination of an element type and a position vector representing an atom position in a lattice vector expression for each atom contained in the crystal lattice a number of times corresponding to the number of contained atoms.

5. The material generation apparatus according to claim 4, wherein
the gene data includes a lattice vector, the number of atoms contained in a crystal lattice, and contained atom information obtained by repeating a combination of an element type and a position vector representing an atom position in a lattice vector expression for each atom contained in the crystal lattice a number of times corresponding to the number of contained atoms, excluding lattice constants (a, b, c, α, β, γ).

6. The material generation apparatus according to claim 1, further comprising:
a structural relaxation calculation unit that performs structural relaxation calculating of calculating a stable position of an atom from a force received by each atom in a crystal structure with respect to a crystal structure of a neighborhood set generated by the mutation unit and the crossing-over unit included in the neighborhood set generator, and correcting gene data of the crystal structure by a calculation result.

7. The material generation apparatus according to claim 1, wherein
an occurrence probability of an operation by the mutation unit and the crossing-over unit included in the neighborhood set generator varies an occurrence probability of each operation depending on the number of atoms inside a crystal structure selected as an operation target.

8. The material generation apparatus according to claim 1, wherein
the crossing-over unit included in the neighborhood set generator is a unit that selects two crystal structures, rotates the crystal structures such as aspects of the both crystal structures are matched with each other by sorting orders of lattice lengths or cross-sectional areas of the respective crystal structures to dispose the crystal structures in an analysis space on a computer, generates one or two random numbers of 0 to 1, cuts the respective crystal structures according to one common random number or two random numbers, and combines the two crystal structures by one internal coordinate expression.

9. The material generation apparatus according to claim 6, further comprising:
a neural network calculation unit that inputs an output of the structural relaxation calculation unit using a deep convolutional neural network configured such that a predictive value of an objective function is output by setting a calculation result of structural relaxation calculation of a crystal structure to an input, and outputs the predictive value of the objective function.

10. The material generation apparatus according to claim 9, wherein
an N-fold cell of a crystal structure is created and divided by an equally spaced grid, a cube around a grid including each atom which is included in a target crystal structure is formed and converted into 1D arrangement data of each cube in a grid arrangement order, and data of the crystal structure is input to the deep convolutional neural network.

11. A material generation method comprising:
generating a current generation crystal structure set of an inorganic material by user definition or random generation at a time of start according to control of a genetic algorithm;
generating a crystal structure of a new neighborhood set by a mutation operation of a crystal structure and a crossing-over operation of a crystal structure from the current generation crystal structure set;
performing structural relaxation calculation on each crystal structure of the neighborhood set;
calculating a feature amount with respect to each crystal structure after the structural relaxation calculation;
calculating a predictive value of an objective function by inputting the calculated feature amount to a regression model;
performing selection and weeding out of a crystal structure based on the predictive value of the objective function;
repeating a loop from the generating of the crystal structure of the neighborhood set to the performing of the selection and weeding out of the crystal structure predetermined number of times;
observing an objective function value by first-principle calculation or with reference to experimental data with respect to a crystal structure set;
updating a regression model based on a result of observing the objective function value; and
determining whether to end or continue processing by determining whether the result of observing the objective function value satisfies a predetermined condition.

12. The material generation method according to claim 11, further comprising:
inputting each crystal structure after the structural relaxation calculation to a deep convolutional neural network to obtain a predictive value of an objective function from an output of the neural network, instead of the calculating of the feature amount and the calculating of the predictive value of the objective function.

* * * * *